United States Patent [19]

Müller

[11] Patent Number: 4,556,052
[45] Date of Patent: Dec. 3, 1985

[54] MEDICAL INSTRUMENT WITH INTERNAL LIGHT SOURCE FOR ILLUMINATING BODY CAVITIES

[75] Inventor: Rolf Müller, Tuttlingen, Fed. Rep. of Germany

[73] Assignee: Gustav Mueller GmbH und Co. KG, Tuttlingen, Fed. Rep. of Germany

[21] Appl. No.: 611,404

[22] Filed: May 17, 1984

[30] Foreign Application Priority Data

May 17, 1983 [DE] Fed. Rep. of Germany ....... 3317831
May 17, 1983 [DE] Fed. Rep. of Germany ....... 3317832

[51] Int. Cl.$^4$ ................................................ A61B 1/06
[52] U.S. Cl. ........................................ 128/11; 128/16; 128/18
[58] Field of Search .............................. 128/11, 16, 18

[56] References Cited
U.S. PATENT DOCUMENTS

3,638,644 2/1972 Reick .................................... 128/16
4,273,112 6/1981 Heine .................................... 128/11

Primary Examiner—William H. Grieb
Attorney, Agent, or Firm—Karl F. Ross; Herbert Dubno

[57] ABSTRACT

A medical instrument, specifically a laryngoscope, has a hollow handle containing a primary or secondary electric battery and a lamp, the latter having a light bulb disposed at the upper end of a detachable head of the handle toward which it is urged by a spring bearing upon the battery from below. The lamp is held in a metallic sleeve surrounded by a dielectric sheath which is snap-fitted into the detachable head; the sheath and the sleeve are axially repressible against the spring force. A speculum is pivoted to that head and is swingable between an idle position alongside the handle and a working position perpendicular thereto. In its working position, a camming projection on the speculum represses the assembly of battery, sheath, sleeve and lamp and closes an energizing circuit for the light bulb through the handle head. The speculum has a channel which terminates short of its tip and accommodates a fiber-optical light guide whose rear end is illuminated by the light bulb in the working position. The channel is bounded by two sheet-metal profiles joined together by arc welding and/or soldering.

20 Claims, 13 Drawing Figures

MEDICAL INSTRUMENT WITH INTERNAL LIGHT SOURCE FOR ILLUMINATING BODY CAVITIES

FIELD OF THE INVENTION

My present invention relates to a medical instrument, such as a laryngoscope, of the type wherein an applicator or speculum is pivotally mounted on a handle and is designed to illuminate an anatomical cavity or recess with the aid of light rays piped from a source inside the handle toward the tip of that applicator.

BACKGROUND OF THE INVENTION

An instrument of this description is known from U.S. Pat. No. 3,638,644 to F. G. Reick. The laryngoscope particularly disclosed in that patent utilizes a solid light guide, in the form of a curved strip of polyacrylate (Lucite or Plexiglas) terminating in a reduced front end at the tip of the applicator and in a broader rear end which in a working position is closely spaced from an aperture at the top of the handle overlying a light bulb. The latter is part of a lamp closely surrounded by a metallic sleeve in direct contact with the metallic shell of the handle which in turn is conductively connected, through a biasing spring at the bottom of that handle, with the negative pole of a battery stack whose positive pole is normally held separated, by means of another spring, from a centrally disposed terminal of the light bulb. When the applicator is swung into its working position, via a pivotal junction linking it with the handle, a pair of feet of that applicator cammingly engage the metallic sleeve in order to repress the lamp against the force of the last-mentioned spring so as to let its central terminal make contact with the positive battery pole whereby the bulb is energized to illuminate the proximal end of the acrylic strip. An abutment rising from the top of the head carries detent balls coacting with recesses on the feet bracketing same in order to index the applicator in its working position.

As noted in that patent, Lucite is a brittle and fragile material wherefore the light-guiding strip has to be supported on the applicator by a depressor blade made from a tough resin, namely polycarbonate. The strip is flanked on one side by a reinforcing rib but is otherwise exposed, except at its rear end where it is shielded by a glare cover.

The described camming mechanism for closing the lamp circuit has the drawback that the light bulb may be accidentally energized, with consequent discharge of the associated batteries, even when the applicator or speculum is in its inoperative or idle position. This could happen, for example, when the bulb is inadvertently repressed by hand or when its sleeve jams in the repressed state after a temporary swing of the applicator into its working position. In case of a burnout, extraction of the bulb from its socket for the purpose of replacement requires the use of a special tool.

OBJECTS OF THE INVENTION

The general object of my present invention is to provide an improved medical instrument of the type referred to, especially a laryngoscope, which obviates the disadvantages of known implements of that sort.

A more particular object is to provide such an instrument with a speculum whose light guide is not made of a brittle material requiring a massive support and which therefore can be manufactured in its entirety from materials other than polycarbonate, preferably from sheet metal.

A related object is to provide a speculum structure by which the light guide, advantageously a bundle of optical fibers, is enclosed over virtually its full length in a protective channel preventing the entry of bacteria into a patient's oral cavity or other recesses to be explored.

A further specific object of my invention is to provide a handle construction which facilitates the extraction of a light bulb and prevents untimely closure of an energizing circuit therefor.

SUMMARY OF THE INVENTION

According to an important feature of my present invention, a medical instrument for the exploration of anatomical cavities, having a speculum pivoted to a hollow handle (considered upright for the purpose of definition) containing a light source and an associated generator of electrical energy approximately as shown in the above-discussed Reick patent, has light-guiding means extending within a lighttight and externally smooth-surfaced channel of the speculum which is bounded by a web and a lower transverse flange of a first profile and by a web and an upper transverse flange of a second profile, the first profile being of generally Z-shaped cross-section while the cross-section of the second profile is of inverted-L shape. The upper transverse flange of the second profile closely adjoins an upper transverse flange of the first profile, being preferably welded or soldered thereto so that these two transverse flanges form a continuous upper surface, while the web of the second profile rests on the lower transverse flange of the first profile to which it may be soldered or welded by a longitudinal seam adjoining the web and flange surfaces without external discontinuities. With the last-mentioned flange extending laterally beyond the web of the second profile, that flange forms a continuous lower surface which is laterally offset from the upper surface; the terms "upper" and "lower", as herein used, apply to a generally horizontal working position of the speculum substantially perpendicular to its upright handle.

When the instrument is designed as a laryngoscope, as in the preferred embodiment more fully described hereinafter, the upper surface is upwardly convex to serve as a support for the palate of the patient whereas the lower surface is downwardly concave to serve as a tongue depressor. For the illumination of a sufficiently wide area of a patient's throat (or, more generally, some other anatomical recess to be explored), the light-guiding means and thus the second profile forming part of its protective channel should terminate short of the tip of the speculum while the first profile may extend lengthwise beyond the front end of the light-guiding means to the tip of the speculum where the two transverse flanges of that first profile advantageously converge. The front end of a fiber bundle serving as the light-guiding means preferably terminates flush with the second profile while being embraced by a ferrule fitting tightly into the channel so as to seal it against possible entry or exit of bacteria. A similar seal may be provided at the rear or tail end of the fiber bundle by a bushing preferably formed with a projecting shoulder.

Pursuant to another important feature of my invention, the handle of the instrument includes not only a cylindrical metallic shell but also a metallic head coaxially threaded into same. In an upright handle position, i.e. with the common axis of the shell and the head generally vertical as will usually be the case when the instrument is being handled by a practitioner, the light source will lie at the top of the head, just below a metallic foot of the speculum which forms with that head the pivotal junction allowing the speculum to be selectively swung between its idle and working positions. The light source is a conventional lamp with a bulb received in a socket, that socket being closely surrounded by a metallic sleeve in conductive contact therewith and thus with a terminal of the bulb filament. In contradistinction to the arrangement of the above-identified Reick patent, however, the metallic sleeve does not contact the shell of the handle but is insulated therefrom by a dielectric sheath enveloping it inside the handle's head. Another terminal of the bulb is in continuous direct contact with a central (positive) pole of a battery, which may be of the primary or of the secondary—i.e. rechargeable—type and could be one of several such batteries stacked as in the Reick patent; the battery or batteries form together with the dielectric sheath, the metallic sleeve and the lamp an assembly which as a whole is axially movable in the handle and is urged upward by spring means disposed in the housing. The foot of the speculum is provided with cam means conductively connected with the head of the handle by their pivotal junction, the cam means engaging the sleeve in the working position of the speculum for closing an energizing circuit through the bulb while repressing the movable assembly against the force of the spring means. Thus, the bulb lights only in that working position to illuminate the aforedescribed light-guiding means, preferably a fiber bundle, extending from the vicinity of the top of the head toward the tip of the speculum. The cam means may be an extension of the aforementioned bushing, e.g. a shoulder-forming collar.

In the event of a rechargeable or storage battery having a pair of prongs which flank the central pole and are insertable into a socket of a source of charging current, these prongs are received in a pair of diametrically opposite clearances of the head. One prong, i.e. the one connected to the negative battery pole, is conductively connected (e.g. by an interposed spring) to the head and thus to the shell of the handle so as to form part of the energizing circuit which is closed when the movable assembly is repressed by the cam means. The head of the handle may be provided with a pair of upstanding ridges bracketing the foot of the speculum, these ridges supporting a pivot pin which is offset from the handle axis and is engaged in a slot of the foot to act as a fulcrum for its swinging motion. The ridges can be further provided with confronting formations which are engageable by indexing means on the foot, such as the detent balls mounted on the handle abutment of the Reick laryngoscope but with an inverted arrangement, for yieldably retaining the speculum in its working position.

BRIEF DESCRIPTION OF THE DRAWING

The above and other features of my invention will now be described in detail with reference to the accompanying drawing in which.

SPECIFIC DESCRIPTION

Figure 1:
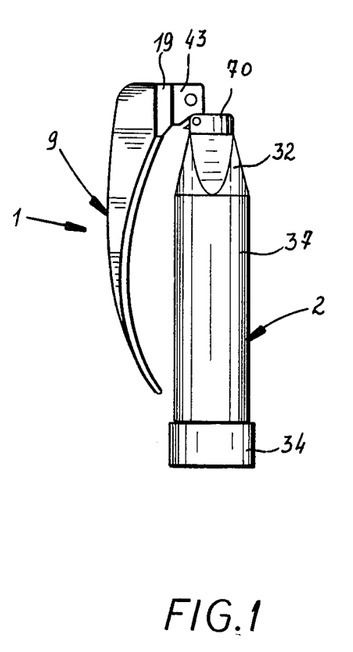
FIG. 1 is a side-elevational view of a laryngoscope embodying my invention, with a speculum shown in its idle position alongside an upright handle.
Figure 2:
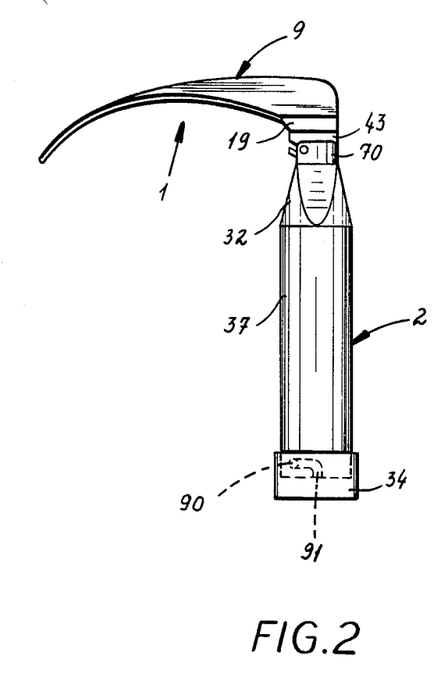
FIG. 2 is a view similar to FIG. 1, showing the speculum in its working position.
Figure 3:
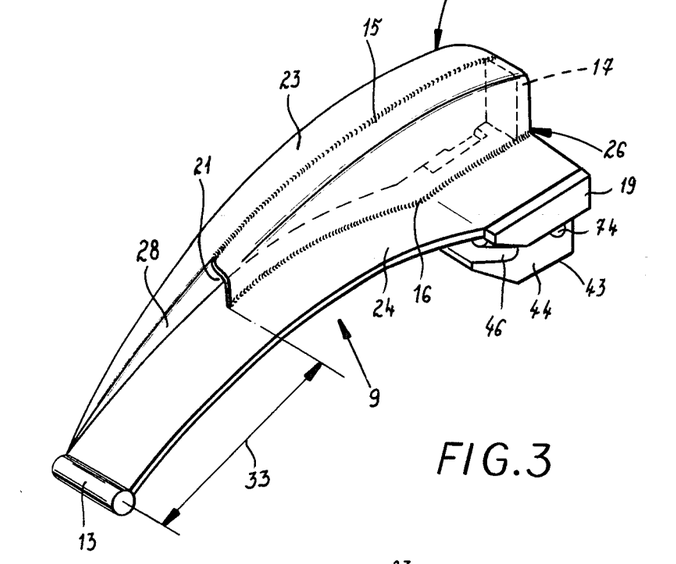
FIG. 3 is a perspective view of the speculum drawn to a larger scale.

In FIGS. 1 and 2 I have shown a laryngoscope 1 resembling the appliance disclosed in the above-identified Reick patent. The instrument comprises an upright, generally cylindrical handle 2 to which a speculum 9 is pivoted for selective swinging between an idle or inoperative position, FIG. 1, and a working or operative position, FIG. 2. The handle 2 is longitudinally subdivided into a tubular shell 37 and an upwardly tapering tubular head 32 screwed onto the upper end of that shell as more fully described hereinafter. The lower end of the shell 37 is closed by a cap 34 secured thereto via a bayonet coupling which is formed by studs 90 engaged in slots 91 (only one of each shown).

Figure 4:
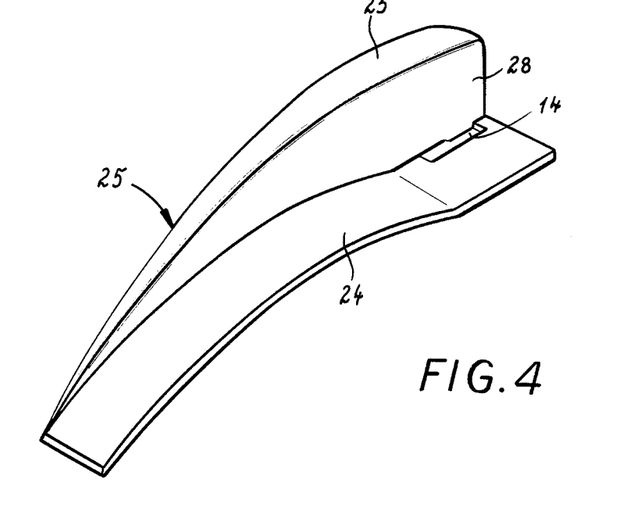
FIG. 4 is a perspective view similar to FIG. 3, showing a Z-section profile forming part of the speculum.
Figure 5:
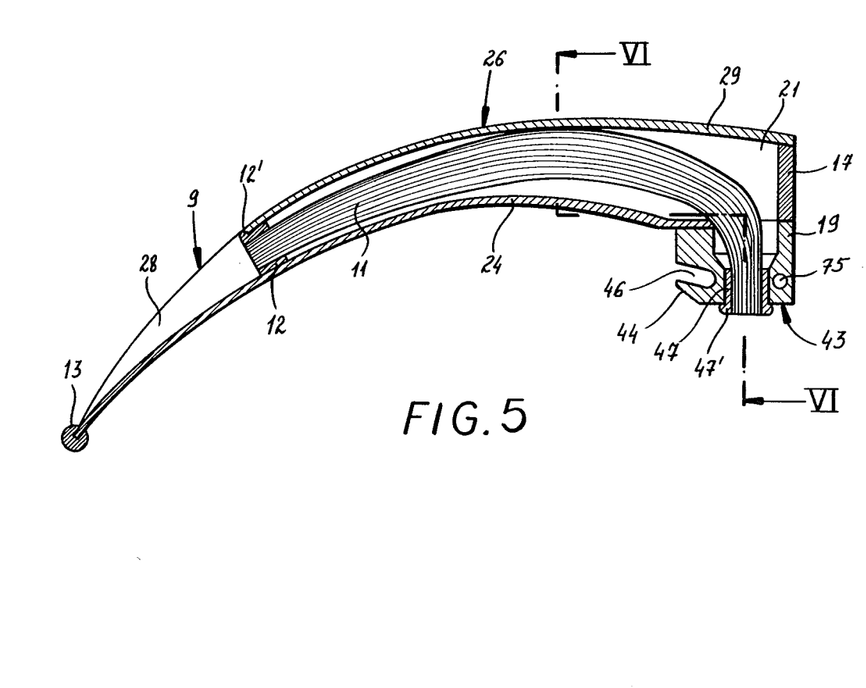
FIG. 5 is a side-elevational view of the speculum taken substantially on the line V—V of FIG. 6.
Figure 6:
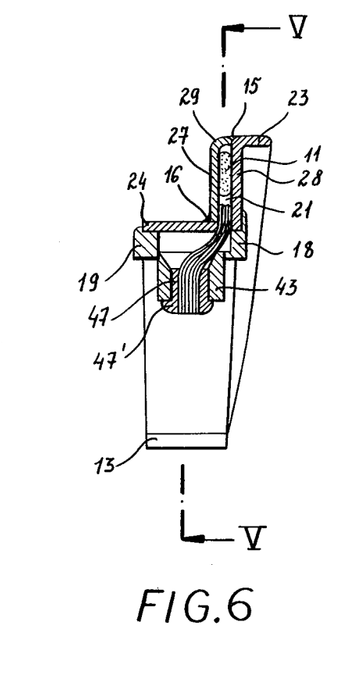
FIG. 6 is a cross-sectional view taken substantially on the line VI—VI of FIG. 5.

Details of speculum 9 are shown in FIGS. 3-6. The speculum consists, essentially, of a first sheet-metal profile 25 of generally Z-shaped cross-section, a second sheet-metal profile 26 of inverted-L-shaped cross-section, and a foot 43 fitted onto profile 25. This profile, illustrated by itself in FIG. 4, comprises a cantilevered upper transverse flange 23, a lower transverse flange 24 and an upstanding web 28 interconnecting these flanges. The upper flange 23 narrows progressively toward the front end of the profile where it joins the lower flange 24, which is of substantially constant width greatly exceeding the maximum width of flange 23. The web 28, consequently, progressively decreases in height toward that front end. A slot-shaped aperture 14 near the rear end of flange 24 gives passage to a bundle 11 of optical fibers which is confined for the most part in a lighttight channel 21 that is bounded by web 28 and flange 24 of profile 25 and by a web 27 and a transverse flange 29 of profile 26. The two flanges 23 and 29 are flush with each other and are united by an arc-welding seam 15 which has been suitably leveled off, as best seen in FIG. 6, to let these two flanges form a continuous upper surface that is upwardly convex to serve as a palate support when the speculum is introduced into the mouth of a patient whose throat is to be explored. In the assembled speculum illustrated in FIG. 3, the web 24 terminates in a small transverse cylinder 13 designed to prevent any part of the patient's mouth from coming into contact with a sharp edge; web 24 is downwardly concave to act as a tongue depressor.

The correspondingly curved lower edge of web 27 rests on the flange 24 to which it is soldered along a seam 16 with a substantial initial excess of solder. That seam, again as best seen in FIG. 6, is also carefully machined and polished so as to form, in its cross-section, a small arc faired smoothly into the exposed surfaces of the web and the flange.

As seen in FIG. 5, the fiber bundle 11 terminates at the front end of profile 26 where that bundle is embraced by a ferrule 12 fitting tightly into the channel 21. The ferrule has, of course, the same rectangular cross-section as the channel 21 at that front end. At its upper edge and its outer lateral edge, ferrule 12 is formed with a lip 12' of rounded cross-sectional contour bearing upon the front end of profile 26 to mask the sharp edges of the profile at that end, again without any external discontinuity. The ferrule thus has the dual purpose of firmly supporting the front end of the fiber bundle and of sealing the channel at that end against a possible entry or exit of bacteria which could be transferred to the mouth of the patient. In fact, the entire portion of the speculum 9 receivable in the patient's mouth is externally smooth-surfaced without any hard-to-clean crevices in which microorganisms could collect.

At its rear, channel 21 is closed by a back plate 17 inserted between flange 29 and foot 43. The sides of that foot are formed in part by two cheeks 18 and 19 which are recessed to receive the flange 24 of profile 25 between them. The tail end of fiber bundle 11, which passes into the foot 43 through the slot 14 shown in FIG. 4, is tightly gripped by a cylindrical bushing 47 which is firmly seated in a vertical passage of that foot and has a collar 47' so as to form a shoulder bearing from below upon the underside of the foot. The latter is further provided with a hook 44 bounding a slot 46 which is open toward the tip of speculum 9 and slopes upward in the working position of FIG. 5. Slot 46 is designed to receive a pivot pin 45 of handle head 32, illustrated in FIG. 7, which serves as a fulcrum for the swing of the speculum between the idle and working positions respectively shown in FIGS. 1 and 2.

Figures 7, 8:
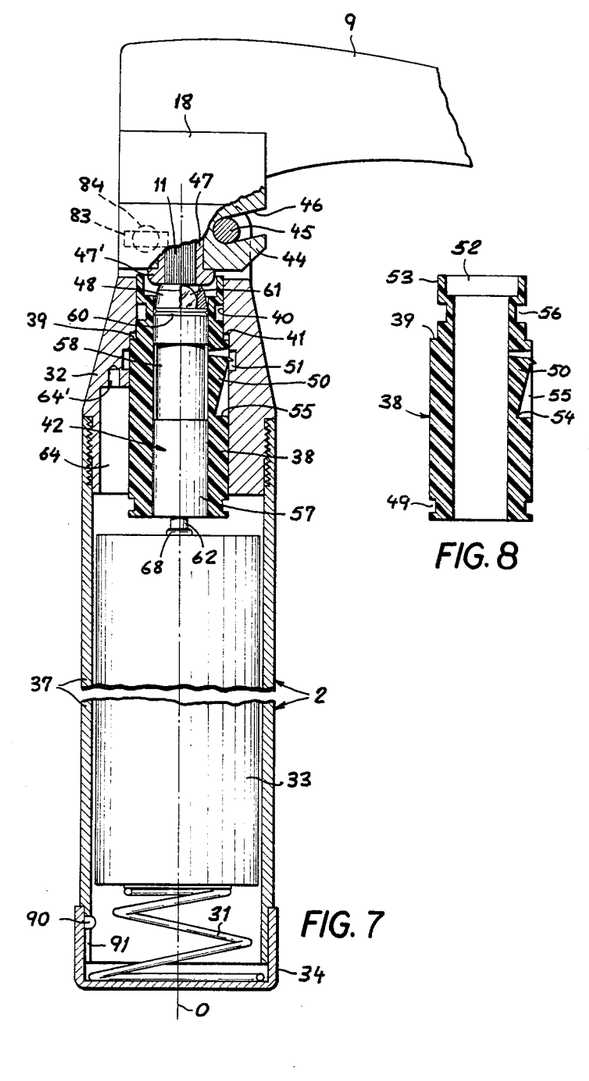
FIG. 7 is an elevational view, partly in section, of the instrument handle and an adjoining portion of the speculum in its working position, drawn to approximately the same scale as FIGS. 3-6.
FIG. 8 is an axial sectional view of a dielectric sheath forming part of an assembly which is axially movable in the handle of the instrument shown in FIG. 7.
Figure 10:
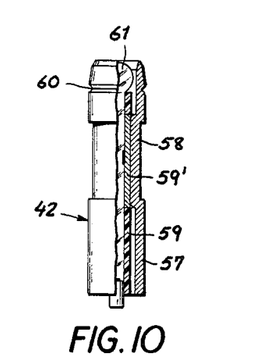
FIG. 10 is an elevational view, partly in section, of a lamp and a surrounding metallic sleeve forming part of the same assembly.

From FIG. 7 it will further be noted that, in the working position illustrated there, the collar 47' of bushing 47 penetrates partly into the top of head 32 so that the end of fiber bundle 11 lies directly above a bulb 61 which, together with a lamp socket 59 shown in FIG. 10, serves as a light source for the illumination of a patient's throat by way of that bundle. The lamp socket 59, consisting for the most part of dielectric resinous material, has a conductive surface portion 59' in contact with one terminal of the filament of bulb 61 whose other terminal 62 extends along the axis O of handle 2 and is well separated from a metallic sleeve 42 surrounding that socket. Sleeve 42 has a top section 48 provided with an annular groove 60 imparting to it a certain degree of elastic deformability. A constricted middle section 58 of that sleeve engages the conductive portion 59' of the lamp socket which adjoins a bottom section 59 of the same diameter as top section 48.

Terminal 62 of bulb 61, well separated from sleeve 42, is in direct contact with a central positive pole of a battery 33 disposed in the lower part of handle 2, i.e. inside shell 37 below the level of head 32. A coil spring 31 at the bottom of that shell, supported by cap 34, bears upon the underside of battery 33 to bias it upward while also establishing a conductive connection between shell 37 and the negative battery terminal which in the usual manner is constituted by a metallic housing enclosing the electrochemically active material.

Figure 9:
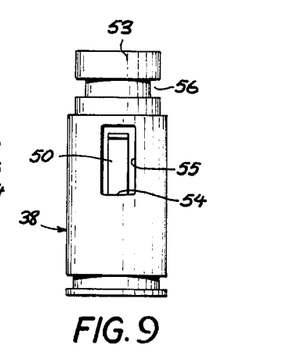
FIG. 9 is an elevational view of the sheath illustrated in FIG. 8.
Figures 11, 12, 13:
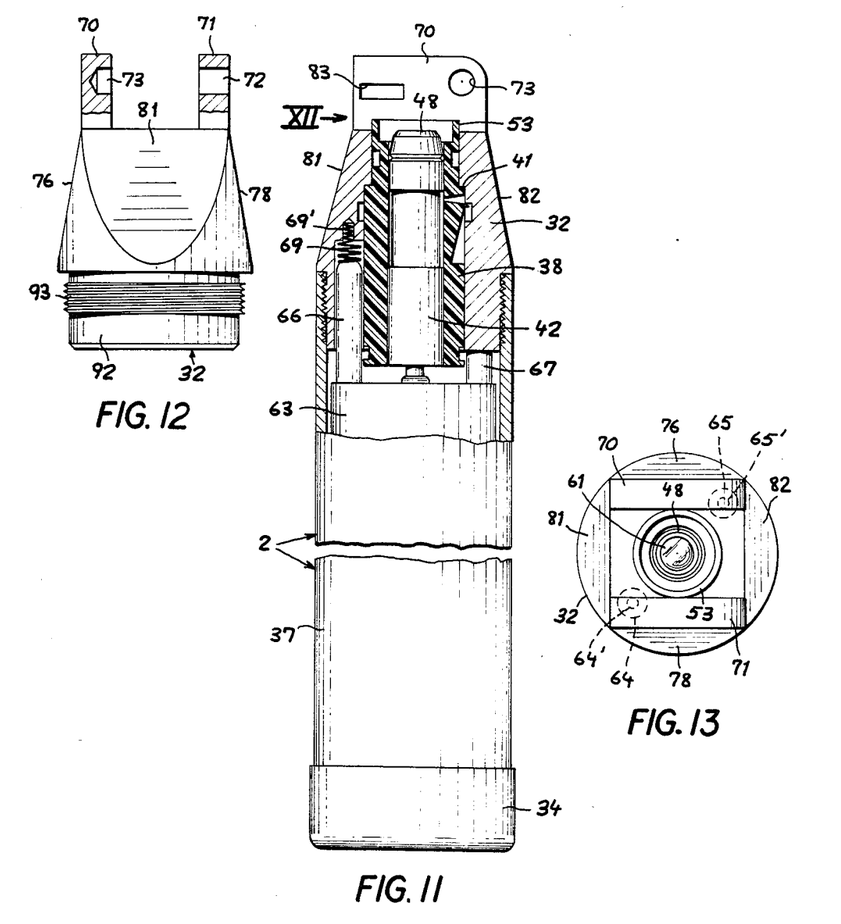
FIG. 11 is an axial sectional view of the instrument handle, showing a somewhat modified assembly contained therein.
FIG. 12 is an elevational view, partly in section, of a head portion of the instrument handle as seen in the direction of arrow XII of FIG. 11.
FIG. 13 is a top view of the handle and its head shown in FIGS. 7, 11 and 12.

Sleeve 42 is embraced by a tubular sheath 38 of dielectric material which is snap-fitted into a central bore 40 of head 32 with the aid of one or more yieldable barbs 50 projecting into an inner annular recess 51 of this head. Each barb is fastened to the remainder of the sheath by a reduced part 54 and is movable in a window 55 as best seen in FIGS. 8 and 9. An annular shoulder 39 of sheath 38 (see FIG. 8) confronts an internal shoulder 41 of bore 40 against which it is pressed by spring 31 (see FIG. 11) when the speculum 9 is in its alternate (idle) position. Recess 51 is wide enough to let the barb or barbs 50 move therein axially between an elevated position, defined by shoulders 39 and 41, and a depressed position into which the assembly consisting of lamp 59, 61, sleeve 42, sheath 38 and battery 33 is lowered by a camming engagement between the collar 47' of bushing 47 and the top section 48 of sleeve 42 when the speculum 9 is swung about pivot pin 45 into the working position shown in FIG. 7. In that position, the speculum is indexed by detent balls 84 projecting under spring pressure from a transverse bore 75 of foot 43 (FIG. 5) and engaging in depressions 83 of a pair of parallel ridges 70, 71 which rise from the top of head 32 as best seen in FIGS. 11–13. In order to prevent the balls 84 from dropping out of bore 75, they may be retracted more than halfway into that bore (against an interposed coil spring) and the rims of the bore may be somewhat peened over to reduce their diameter.

Light bulb 61 may be of the type described in the Reick patent, with a lens at its tip. That tip projects partly into a space 52 bounded by a cup-shaped upper end 53 of sheath 38 lying above an outer annular recess 56 of that sheath which imparts to the cup 53 a certain flexibility in order that the camming extension 47' of bushing 47 may pass readily thereover even in the event of some dimensional inaccuracies.

As seen in FIG. 12, ridges 70 and 71 are respectively provided with a blind bore 73 and with a throughgoing bore 72 into which the pivot pin 45 is to be inserted with a tight fit. The two ridges lie at opposite sides of a substantially square plateau which tops off the head 32 whose cylindrical periphery is partly cut away by four flat lands 76, 78 and 81, 82 adjoining respective sides of the plateau toward which they converge.

Head 32 is further provided with two diametrically opposite, axially extending bores 64, 65 (see also FIG. 13) which are functionless in the handle of FIG. 7 where the generator of electrical energy is a primary battery 33 or possibly a stack of several such batteries as shown in the Reick patent. I may, however, replace that primary battery by a secondary or storage battery 63, shown in FIG. 11, which has a charging attachment with a pair of prongs 66, 67 designed to be plugged into a current source such as a wall socket when the battery is to be recharged. In the assumption that prong 66 is a ground lead, connected directly to the battery housing serving as its negative pole, and that prong 67 is connected via an internal step-down and rectification circuit to a central positive pole such as that shown at 68 in FIG. 7, these prongs are respectively inserted into bores 64 and 65. While prong 67 is inactive, prong 66 bears in bore 64 upon a contact-intensifying conductive coil spring 69 which has a reduced extremity 69' received in a similarly reduced upward extension 64' of that bore; the other bore 65 has a like extension 65', unused in this instance, as indicated in FIG. 13. Thus, the negative battery pole is again conductively connected with shell 37 and head 32 of handle 2, as is the case with battery 33 of FIG. 7. Here, too, bulb terminal 62 is in continuous contact with the central positive battery pole.

In both cases, therefore, a swing of speculum 9 into its working position completes an energizing circuit through bulb 61 which extends from terminal 62 to the positive battery pole, thence from the negative battery pole to head 32 and then via ridges 70, 71 and pivot pin 45 to foot 43 whose bushing 47 completes the circuit to the other bulb terminal by way of collar 47' and sleeve 42. It will further be apparent that with speculum 9 inoperatively positioned, as in FIG. 1, there is no possibility of accidental completion of this energizing circuit.

As clearly shown in FIG. 12, head 32 has a tubular neck 92 with a fine thread 93 by which it is screwed into the upper part of shell 37. Unscrewing the head 32 from the shell 37 thus allows the subassembly of sheath 38, sleeve 42 and lamp 59, 61 to be extracted therefrom to facilitate a replacement of bulb 61, or possibly of the entire subassembly, if necessary.

From the foregoing description it will be apparent that I have disclosed a medical instrument for the purpose set forth which is of relatively simple structure, consisting of a limited number of parts which can be readily disassembled and reassembled. Its metallic speculum is easy to clean and sterilize after detachment from the handle, which is conveniently accomplished in the idle position of FIG. 1.

I claim:

1. A medical instrument for the exploration of anatomical cavities, comprising:
    a hollow upright handle;
    an elongate speculum pivoted to an upper end of said handle for selective swinging into an idle position alongside said handle and a substantially horizontal working position generally perpendicular thereto;
    a light source and an associated generator of electrical energy disposed next to each other in said handle, said light source being positioned at said upper end for emitting light from the top of said handle;
    cam means on said speculum effective in said working position to close an energizing circuit connecting said light source across said generator; and
    light-guiding means in said speculum extending in said working position from the vicinity of said top toward a tip of said speculum in a lighttight and externally smooth-surfaced channel bounded by a web and a lower transverse flange of a first profile of generally Z-shaped cross-section and by a web and an upper transverse flange of a second profile of inverted-L-shaped cross-section closely adjoining said first profile, an upper transverse flange of said first profile being flush with the upper transverse flange of said second profile, the web of said second profile resting on the lower transverse flange of said first profile.

2. An instrument as defined in claim 1 wherein said upper transverse flanges form in said working position a continuous upper surface, the lower transverse flange of said first profile extending laterally beyond the web of said second profile and forming a continuous lower surface laterally offset from said upper surface and provided with an aperture traversed by said light-guiding means.

3. An instrument as defined in claim 2 wherein said profiles are metallic, said upper flanges being joined together by a weld seam, the web of said second profile being joined without external discontinuities to the lower transverse flange of said first profile by a longitudinally extending seam of solder.

4. An instrument as defined in claim 2, designed as a laryngoscope, wherein said upper surface is upwardly convex to serve as a palate support, said lower surface being downwardly concave to serve as a tongue depressor.

5. An instrument as defined in claim 2 wherein said second profile terminates short of the tip of said speculum, said first profile extending lengthwise beyond said second profile with the transverse flanges thereof converging at said tip.

6. An instrument as defined in claim 5 wherein said light-guiding means is a fiber bundle terminating at a front end of said second profile, said fiber bundle being embraced at said front end by a ferrule fitting tightly into said channel.

7. An instrument as defined in claim 6 wherein said ferrule has a rounded lip bearing endwise upon said second profile.

8. An instrument as defined in claim 2 wherein said first profile is fitted onto an underlying foot having a generally vertical passage communicating with said aperture, said light-guiding means extending through said passage toward said top, said foot having a hook engageable with a pivot pin on said handle for enabling the swinging of said speculum between said idle and working positions.

9. An instrument as defined in claim 8 wherein said foot further has indexing means engageable with a coacting formation on said handle for yieldably retaining said speculum in said working position.

10. An instrument as defined in claim 8 wherein said light-guiding means is a fiber bundle with an end proximal to said top encased in a metallic bushing having a projection forming said cam means.

11. An instrument as defined in claim 10 wherein said handle comprises a metallic shell with a detachable metallic head forming said top and carrying said pivot pin, said light source being a bulb in a lamp socket within said head surrounded by a metallic sleeve in conductive contact with said lamp socket but spaced from a terminal of said bulb, said generator being at least one battery with a central pole in continuous direct contact with said terminal and an outer pole conductively connected with said shell, further comprising a dielectric sheath surrounding said sleeve and insulating same from said head, said battery and said lamp socket being spring-biased together with said sheath and said sleeve toward said top, said bushing being conductively connected through said foot with said head and coming to bear with said projection in said working position upon said sleeve for closing said energizing circuit while repressing said lamp socket together with said sheath and said battery against the biasing spring force.

12. An instrument as defined in claim 8 wherein said channel is closed by a rear plate above said foot.

13. An instrument as defined in claim 1 wherein the upper transverse flange of said first profile is narrower than the lower transverse flange thereof.

14. A medical instrument for the exploration of anatomical cavities, comprising:

a hollow handle including a cylindrical metallic shell and a metallic head threaded onto said shell, said head and said shell being centered on a substantially vertical axis, the interior of said shell opening onto the top of said head;

an elongate speculum having a metallic foot linked with said head by a pivotal junction for selective swinging into an idle position alongside said handle and a working position generally perpendicular thereto;

an assembly axially movable in said handle including battery means inside said shell with an outer pole conductively connected to said shell and with a central pole extending along said axis, a lamp with a socket and a light bulb disposed close to said top in said head, a metallic sleeve closely surrounding said socket in conductive contact therewith, a terminal of said light bulb being spaced from said sleeve and in continuous direct contact with said central pole, and a dielectric sheath surrounding said sleeve for insulating same from said head;

spring means in said housing axially urging said assembly upward;

metallic cam means on said foot conductively connected with said head through said pivotal junction, said cam means engaging said sleeve in said working position for closing an energizing circuit from said battery through said light bulb while repressing said assembly against the force of said spring means; and light-guiding means extending from the vicinity of said top within said speculum toward a tip thereof for illuminating an anatomical part to be explored.

15. An instrument as defined in claim 14 wherein said battery means is a storage battery provided with a pair of prongs insertable into a socket of a source of charging current, said prongs flanking said central pole, said outer pole being one of said prongs, said head being provided with a pair of bores accommodating said prongs.

16. An instrument as defined in claim 14 wherein said sheath is provided with barb means receivable with a snap fit in a recessed inner surface portion of said head.

17. An instrument as defined in claim 14 wherein said head is provided with a pair of upstanding ridges bracketing said foot, said ridges supporting a pivot pin offset from said axis engaged in a slot of said foot as a fulcrum therefor, said ridges being further provided with confronting formations engageable by indexing means on said foot for yieldably retaining said speculum in said working position.

18. An instrument as defined in claim 14 wherein said light-guiding means is a fiber bundle with an end proximal to said top encased in a metallic bushing received in said foot, said cam means being an extension of said bushing.

19. An instrument as defined in claim 18 wherein said extension is a collar bearing from below upon the underside of said foot.

20. An instrument as defined in claim 14 wherein said speculum comprises a tongue depressor.

* * * * *